(12) United States Patent
Wodnicki et al.

(10) Patent No.: US 9,525,852 B2
(45) Date of Patent: Dec. 20, 2016

(54) SYSTEMS AND METHODS FOR EMBEDDED IMAGING CLOCKING

(71) Applicant: General Electric Company, Schenectady, NY (US)

(72) Inventors: Robert Gideon Wodnicki, Niskayuna, NY (US); Sora Kim, Niskayuna, NY (US); Ansas Matthias Kasten, Niskayuna, NY (US); Kevin Coombs, Skaneateles, NY (US); Clark Alexander Bendall, Syracuse, NY (US); Jonathan David Short, Saratoga Springs, NY (US)

(73) Assignee: General Electric Company, Schenectady, NY (US)

( * ) Notice: Subject to any disclaimer, the term of this patent is extended or adjusted under 35 U.S.C. 154(b) by 669 days.

(21) Appl. No.: 13/958,209

(22) Filed: Aug. 2, 2013

(65) Prior Publication Data

US 2015/0035967 A1 Feb. 5, 2015

(51) Int. Cl.
*H04N 7/18* (2006.01)
*H04N 5/232* (2006.01)
(Continued)

(52) U.S. Cl.
CPC .......... *H04N 7/183* (2013.01); *H04N 5/23203* (2013.01); *H04N 5/3765* (2013.01); *A61B 1/045* (2013.01); *H04N 2005/2255* (2013.01)

(58) Field of Classification Search
CPC ............ A61B 1/00009; A61B 1/00052; H04N 5/3765
See application file for complete search history.

(56) References Cited

U.S. PATENT DOCUMENTS 3,978,284 A * 8/1976 Yoshino ............. H04N 1/00098
348/24
8,248,464 B2 8/2012 Takahashi
(Continued)

FOREIGN PATENT DOCUMENTS

EP 2249533 A1 11/2010
EP 2254296 A2 11/2010
EP 2575352 A1 4/2013

OTHER PUBLICATIONS

'A 2.0 Gb/s Clock-Embedded Interface for Full-HD 10-Bit 120 Hz LCD Drivers With 1/5-Rate Noise-Tolerant Phase and Frequency Recovery', Yamaguchi, K., IEEE Journal of Solid-State Circuits, vol. 44, Issue 12, Dec. 2009.

(Continued)

*Primary Examiner* — Michael Teitelbaum
(74) *Attorney, Agent, or Firm* — Joseph F. Harding; The Small Patent Law Group, LLC

(57) ABSTRACT

An embedded imaging system in one embodiment includes an encoding module, an imaging module, and a cable. The encoding module is disposed proximate to a proximal end of the system, and is configured to encode frame synchronizing information into timing information comprising a reference clock. The imaging module is disposed proximate the distal end, and includes an image capture device configured to obtain imaging information and a decoding module. The decoding control module is configured to obtain the timing information, to decode the timing information to obtain recovered frame synchronizing information, and to control the image capture device using the recovered frame synchronizing information. The cable is interposed between the proximal end and the distal end, and is configured for passage therethrough of the timing information and the imaging information.

13 Claims, 6 Drawing Sheets

(51) Int. Cl.
*H04N 5/376* (2011.01)
*H04N 5/225* (2006.01)
*A61B 1/045* (2006.01)

(56) References Cited

U.S. PATENT DOCUMENTS

| | | | |
|---|---|---|---|
| 8,368,749 B2 | 2/2013 | Lambdin et al. | |
| 2001/0022612 A1 | 9/2001 | Higuchi et al. | |
| 2005/0179782 A1* | 8/2005 | Endo | H04N 5/23203 348/207.99 |
| 2009/0213212 A1 | 8/2009 | Nakamura | |
| 2009/0216080 A1* | 8/2009 | Nakamura | H04N 5/23203 600/109 |
| 2010/0296589 A1* | 11/2010 | Maeda | H04L 25/4917 375/257 |
| 2011/0298908 A1 | 12/2011 | Murakami | |
| 2012/0323073 A1 | 12/2012 | Azuma et al. | |
| 2013/0012777 A1 | 1/2013 | Baum et al. | |

OTHER PUBLICATIONS

'A Highly Parallel and Scalable CABAC Decoder for Next Generation Video Coding', Sze V., IEEE Journal of Solid-State Circuits, vol. 47, Issue 1, Jan. 2012.

'A High-Resolution Time-to-Digital Converter Based on Multi-Phase Clock Implement in Field-Programmable-GateArray', Zhoujiancheng, Y., 2012 18th IEEE-NPSS Real Time Conference (RT), Jun. 2012.

International Search Report and Written Opinion issued in connection with corresponding PCT Application No. PCT/US2014/046181 dated Jan. 9, 2015.

Anonymous, "Pulse-width modulation", Jul. 25, 2013.

International Invitation to Pay Additional Fees issued in connection with corresponding PCT Application No. PCT/US2014/046181 on Oct. 15, 2014.

\* cited by examiner

SYSTEMS AND METHODS FOR EMBEDDED IMAGING CLOCKING

BACKGROUND

Embedded imaging systems, such as boroscopes or endoscopes, may be used to view imaging information obtained within a volume of interest that may otherwise be difficult to access or view. For example, an endoscope may be inserted into the body of a patient for viewing an internal structure and/or process of the patient. As another example, a boroscope may be used to view images of difficult to access portions of a machine, building, or other structure (e.g., an interior portion of a length of piping or tubing). The portion of the embedded imaging system inserted into the volume of interest may be subject to size (e.g., diameter) restrictions, as too large a device may not be able to be inserted into certain volumes.

Such devices may use a solid state device, such as a charge coupled device (CCD), to capture images within a volume of interest. However, CCDs, for example, may require framing information that is generated off-chip, thus resulting in increased size and/or cost requirements if such information is generated at the distal end of an embedded image system. Difficulties and/or challenges of providing embedded imaging systems of appropriate size may be exacerbated in applications utilizing increased resolution imaging techniques, such as high definition (HD).

For example, in embedded imaging applications it may be useful to have an efficient clocking scheme to drive an image capture device. However, in a boroscope, for instance, the cross-sectional diameter of a wiring harness may be subject to size guidelines or requirements regarding the number and/or size of cables with the wire harness to be limited. Additionally, the available volume for clocking solutions on a portion of the boroscope configured to be inserted within a volume of interest may be limited due to a small size of an imaging head of a cable or harness. If clocks are generated at a portion of the boroscope configured to be outside of the volume of interest and transmitted through the cable or harness, the cable or harness may need to be quite large to transmit such clocks, for example if the clocks are at relatively high frequencies, such as frequencies associated with high resolution (e.g., HD) applications.

BRIEF DESCRIPTION

In one embodiment, an embedded imaging system is provided including an encoding module, an imaging module, and a cable. The encoding module is disposed proximate to a proximal end of the system. The proximal end is configured to be positioned outside of a volume of interest during imaging within the volume of interest by the embedded imaging system. The encoding module is configured to encode frame synchronizing information for controlling electronics disposed proximate a distal end of the system. The distal end is configured to be positioned within the volume of interest during imaging of the volume of interest. The encoding module is configured to encode the frame synchronizing information into timing information comprising a reference clock. In some embodiment, the reference clock may have a frequency lower than a frequency of the frame synchronizing information. The imaging module is disposed proximate the distal end, and includes an image capture device and a decoding module. The image capture device is configured to obtain imaging information of at least a portion of the volume of interest. The decoding control module is configured to obtain the timing information, to decode the timing information to obtain recovered frame synchronizing information corresponding to the frame synchronizing information encoded by the encoding module, and to control the image capture device using the recovered frame synchronizing information. The cable is interposed between the proximal end and the distal end, and is configured for passage therethrough of the timing information from the proximal end to the distal end, and for passage therethrough of the imaging information from the distal end to the proximal end.

In another embodiment, a method is provided including generating frame synchronizing information at one or more processing units disposed proximate a proximal end of an embedded imaging system. The proximal end is configured to be positioned outside of a volume of interest during imaging within the volume of interest by the embedded imaging system. The frame synchronizing information is configured to provide framing information for controlling an image capture device disposed proximate a distal end of the embedded imaging system. The distal end is configured to be positioned within the volume of interest during imaging of the volume of interest. The method also includes encoding, at the one or more processing units disposed proximate the proximal end of the embedded imaging system, the frame synchronizing information into timing information that includes a reference clock having a frequency lower than a frequency of the frame synchronizing information. Also, the method includes transmitting the timing information from the proximal end to the distal end via a cable interposed between the proximal end and the distal end. Further, the method includes decoding, at one or more processing units disposed proximate the distal end of the embedded imaging system, the timing information to obtain recovered frame synchronizing information corresponding to the frame synchronizing information. The method also includes controlling the image capture device to obtain imaging information using the recovered frame synchronizing information.

In another embodiment, a tangible and non-transitory computer readable medium is provided. The computer readable medium includes one or more computer software modules configured to direct one or more processors to generate, proximate a proximal end of an embedded imaging system, frame synchronizing information. The proximal end is configured to be positioned outside of a volume of interest during imaging within the volume of interest by the embedded imaging system. The frame synchronizing information is configured to provide framing information for controlling an image capture device disposed proximate a distal end of the embedded imaging system. The distal end is configured to be positioned within the volume of interest during imaging of the volume of interest. The one or more computer software modules are also configured to direct the one or more processors to encode, proximate the proximal end, the frame synchronizing information into timing information. The timing information includes a reference clock having a frequency lower than a frequency of the frame synchronizing information. Further, the one or more computer software modules are configured to direct the one or more processors to transmit the timing information from the proximal end to the distal end via a cable interposed between the proximal end and the distal end. The one or more computer software modules are also configured to direct the one or more processors to decode, proximate the distal end of the embedded imaging system, the timing information to obtain recovered frame synchronizing information corresponding to the frame synchronizing information. Also, the one or more computer software modules are configured to direct the one or more processors to control the image capture device to obtain imaging information using the recovered frame synchronizing information.

DETAILED DESCRIPTION

Figure 1:
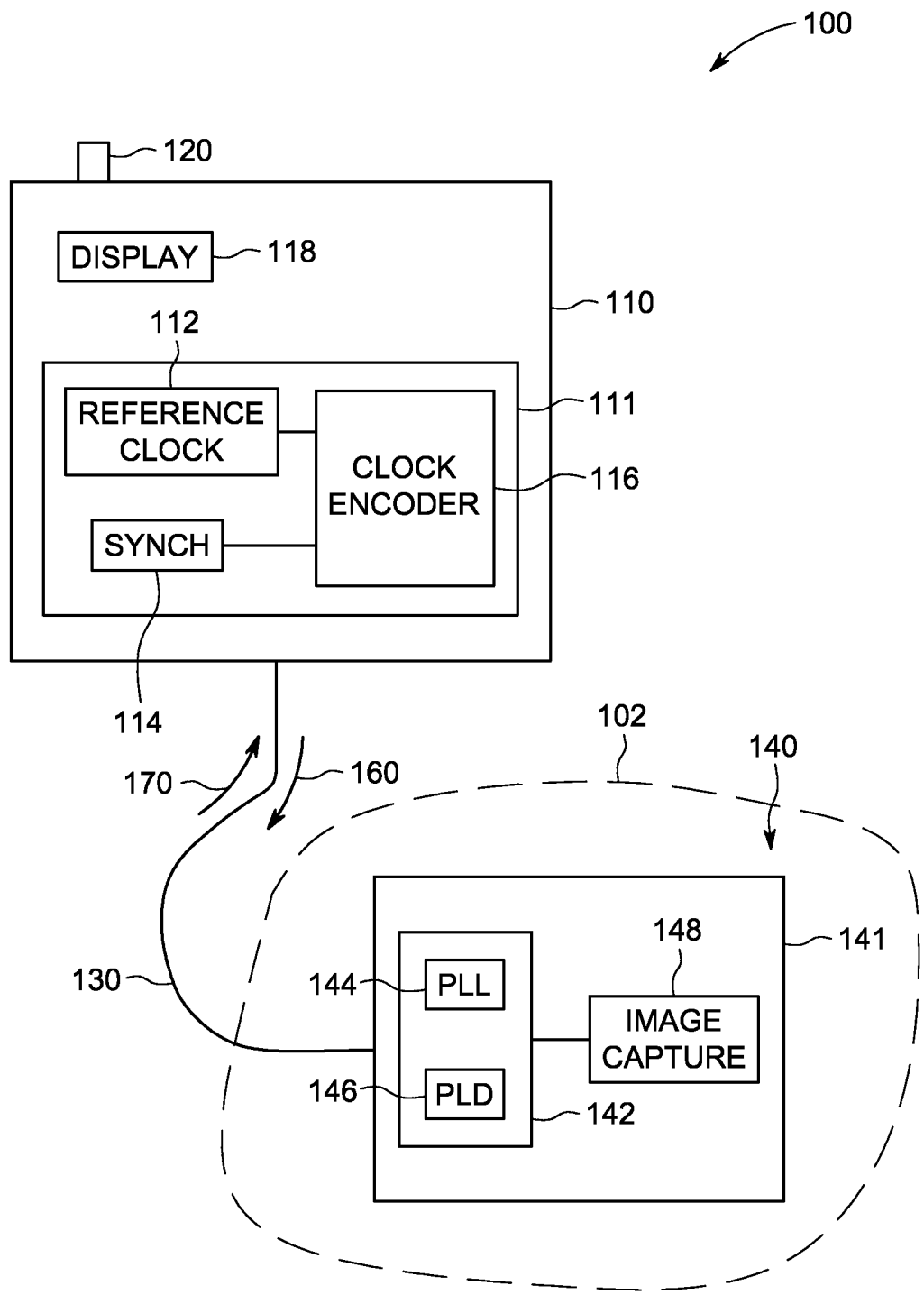
FIG. 1 is a schematic block diagram of an embedded imaging system in accordance with various embodiments.

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof. As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Generally, various embodiments provide efficient clocking and framing schemes that may be transmitted over relatively long cables while maintaining clock signal integrity and fitting into limited available spaces. For example, in various embodiments, control data and/or clock signals for an image capture device may be generated on a proximal end of a cable that connects a distally located image capture device to a display system disposed on the proximal end. The control and clock signal may be transmitted from the proximal end to the distal end (e.g., to an image capture device or modules associated therewith disposed on the distal end) over a relatively thin cable with a low channel count using an efficient clock encoding scheme. The encoded signal may have a frequency that is substantially less than the frequency of one or more clock signals used in conjunction with the image capture device. By way of example, the encoded signal frequency may be about 50%, about 33%, about 25%, about 20%, or about 12.5% of the signal used to control the image capture device.

At least one technical effect of various embodiments is reduced size of a cable used to transmit timing and/or command information from a proximal end to a distal end of an embedded imaging system. At least one technical effect of various embodiments is reduced cost, size, and/or complexity of components (e.g., components disposed at a distal end or portion of an embedded imaging system) used to provide clocking signals to and/or control an image capture device. At least one technical effect of various embodiments is the enablement of high resolution (e.g., HD) imaging while preserving a tight diameter (or cross-sectional area) of an existing cable or harness for an embedded imaging system, or comparable cable or harness. At least one technical effect of various embodiments is the provision for the control of functions in a distal side of an embedded imaging system using signals sent from the proximal side using the same cable as timing information for controlling an image capture device.

FIG. 1 provides a schematic view of an embedded imaging system 100 formed in accordance with various embodiments. The imaging system 100 is configured to obtain imaging information from within a volume of interest 102. The imaging system 100 may include or be configured as, for example, a boroscope or an endoscope. For example, in various embodiments, the imaging system 100 may be configured as an endoscope and the volume of interest 102 may be an internal volume of a patient.

In the illustrated embodiment, the embedded imaging system 100 includes a proximal end 110 and a distal end 140 communicably coupled by a cable 130 interposed therebetween. The proximal end 110, or proximal portion, is configured to be positioned or disposed outside of the volume of interest 102 during acquisition of imaging information corresponding to at least a portion of the volume interest 102 by the imaging system 100. The distal end 140, or distal portion, is configured to be positioned or disposed inside of the volume of interest 102 during acquisition of imaging information corresponding to at least a portion of the volume interest 102 by the imaging system 100.

Generally, in various embodiments, the proximal end 110 is configured to provide control information including framing information for controlling an image capture device disposed in the distal end 140. Framing information may be understood as including information for organization and synchronization of information (e.g., pixels) into lines and/or or frames, for example to help ensure that appropriate pixels are correctly positioned and/or oriented, and displayed as a group (e.g., a first group of pixels collected at a first time displayed together, and a second group of pixels collected at a subsequent second time displayed together). Thus, pixels may be appropriately displayed to provide an image corresponding to a given time without including or mixing with information corresponding to a different time.

In various embodiments, the proximal end 110 (e.g., one or more processors disposed proximate the proximal end 110) may be configured to generate framing information having a first, or framing, frequency that is relatively high, for example for high definition (HD) imaging. The proximal end 110 (e.g., one or more processors disposed proximate the proximal end 110) may further be configured to encode the framing information into timing information including a reference clock having a second, or reference frequency, that is substantially lower than the first or framing frequency. For example, the framing frequency may be divisible by an integer (e.g., 2, 3, or 4, among others) to provide the reference frequency. As just one example, the framing frequency may be about 60 MHz and the reference frequency may be about 15 MHz (or 60 MHz/4). The timing information including the reference clock with the encoded framing information may then be transmitted to the distal end 140 via the cable 130. After the distal end 140 has received the timing information (including the encoded framing information), the distal end 140 (e.g., one or more processors disposed proximate the distal end 140) may decode the timing information to obtain recovered framing information, and use the recovered framing information to drive or control image acquisition. For example, the framing information may be used to drive or control a solid state imaging device. As one example, the framing information may be used to drive or control a charge coupled device (CCD).

Imaging information obtained from within the volume of interest 102 via the distal end 140 may then be transmitted through the cable 130 to the proximal end 110. At the proximal end 110, the imaging information may then be processed and/or displayed, for example, using the framing information originally generated at the proximal end 140. For example, in the illustrated embodiment, the imaging system 100 includes a display module 118 disposed proximate to a proximal end of the system. The depicted display module 118 is configured to provide a display to a viewer or user of the imaging system 100. A display may be provided by displaying information, for example on a screen. Alternatively or additionally, a display may be provided by transmitting a signal or other information via a port 120 to an external system or device configured to display information. The port 120 may include network connections or aspects thereof, USB ports (e.g., for accepting a thumb drive), or the like. Thus, in various embodiments timing information 160 (which may include encoded framing information, encoded command information, or the like) may be transmitted from the proximal end 110 to the distal end 140 via the cable 130, and imaging information 170 (which may include imaging information acquired via, for example, a CCD) may be transmitted from the distal end 140 to the proximal end 110.

Figure 2:
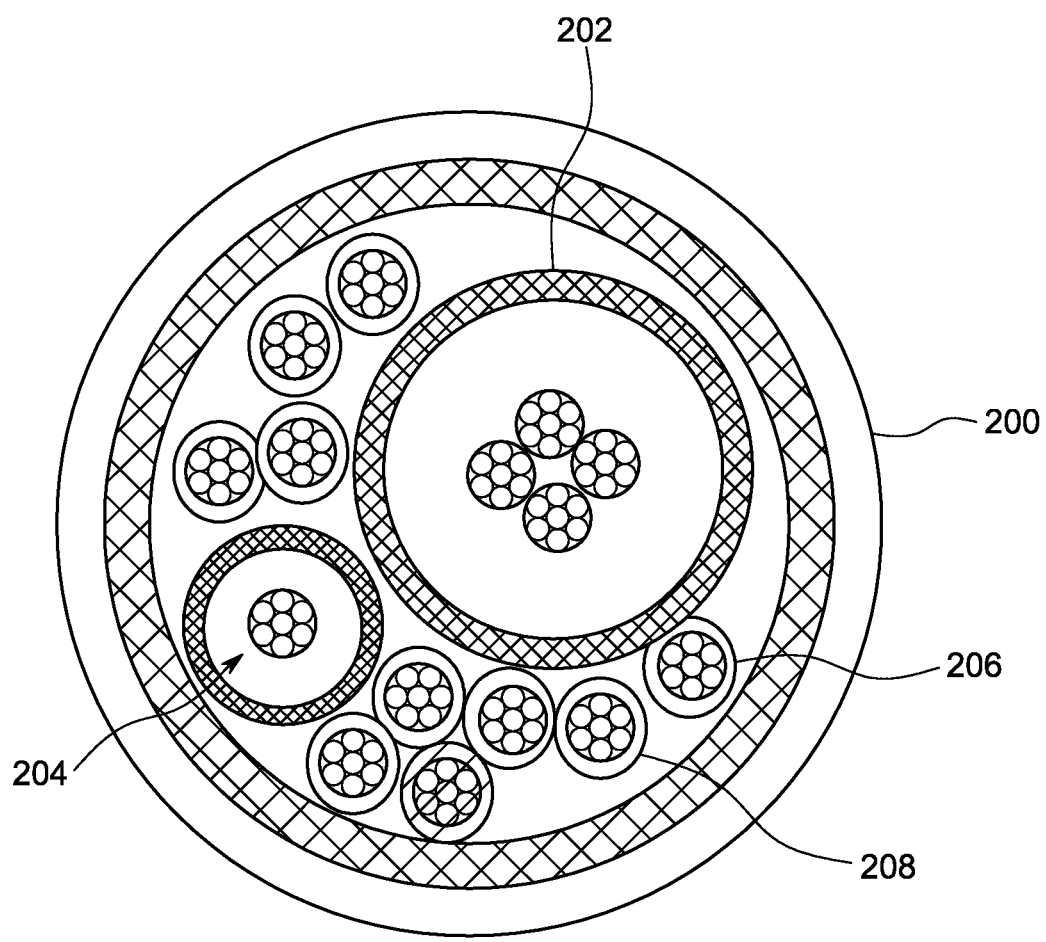
FIG. 2 is a sectional view of a cable in accordance with various embodiments.

FIG. 2 is a sectional view of a cable 200 in accordance with various embodiments. Generally, in various embodiments, the cable 200 is configured to be communicably coupled to and interposed between the proximal end and the distal end of an embedded imaging system, and configured for passage therethrough (e.g., transmission) of timing information for use with an image capture device from the proximal end to the distal end, and for passage therethrough of imaging information acquired by the image capture device from the distal end to the proximal end. The cable 130 may be generally similar in respects to the cable 200. In various embodiments, the cable 200 may be configured to be flexible and/or articulable to help provide versatility and/or adjustment in the positioning of a distal end (e.g., the distal end 140) with respect to a proximal end (e.g., the proximal end 110). In other embodiments, the cable 200 may be configured to be rigidly maintained in a given position to help provide a constant distance and/or orientation of the distal end with respect to the proximal end.

In the illustrated embodiment, the cable 200 may be understood as a wiring harness that in turn includes various wires or cables extending within the cable 200 along the length of the cable 200. Some of the various wires or cables within the cable 200 may be configured as coaxial cables. For example, in the embodiment depicted in FIG. 2, the cable 200 includes a high-definition video cable 202 and a timing information cable 204, both of which are configured as coaxial cables. The high-definition video cable 202 is configured for transmission of imaging information (e.g., imaging information 170) from the distal end 140 to the proximal end 110. For example, in the illustrated embodiment, the high-definition video cable 202 may be configured for transmission of high-definition video signals from a CCD. The timing information cable 204 is configured for transmission of timing information (e.g., timing information 160) including encoded framing information for driving or controlling image acquisition from the proximal end 110 to the distal end 140. The cable 200 may further include various standard wire conductors as shown in FIG. 2. For example, the depicted cable 200 includes a low frequency clock cable 206 and a power supply cable 208. In various embodiments, the cable 200 may include one or more additional low frequency clock cables, power supply cables, or the like.

In embedded imaging applications, such as boroscopes, size (e.g., cross-sectional area) may be at a premium. For example, if the cross-sectional area of the cable 200 becomes too large, a boroscope utilizing the cable 200 may not be usable for a number of applications where imaging equipment is to be inserted through a relatively small space into a volume of interest for imaging within the volume of interest. However, high resolution imaging (e.g., high definition imaging) devices may utilize framing information having relatively high frequencies that require a generally larger diameter timing information cable 204 for transmission, especially over longer distances. Various embodiments allow for the use of high resolution devices by encoding framing information at lower frequencies that may be effectively and efficiently transmitted over a relatively smaller diameter timing information cable 204 than otherwise might be required for a signal sent at a frequency of the framing information.

For example, in the illustrated embodiment, a single timing information cable 204 is depicted. The timing information cable 204 may, in various embodiments, represent a minimum requirement for clocking an image capture device on a distal end of a boroscope utilizing the cable 200 to transmit information between a proximal end and a distal end. The timing information cable 204 may be configured, for example, to transmit a reference clock to be used in obtaining a horizontal clock to drive a CCD. In various embodiments, the depicted timing information cable 204 may be configured as a National Television System Committee (NTSC) or Phase Alternating Line (PAL) capable cable. Use of such a cable in an application where an image capture device is to be run at a faster rate for higher resolution (e.g., about 3 times faster for HD imaging) may require a timing information cable 204 that is about 2.5 times larger in diameter than a timing information cable used for lower resolution applications. To avoid use of the otherwise required larger diameter cable for framing information, various embodiments encode, at the proximal end, the framing information into a lower rate signal that may be transmitted over a smaller diameter cable, and subsequently, at the distal end, decode the transmitted signal to recover the framing information at the higher rate for use with the image capture device. Thus, an embedded imaging system that provides higher resolution (e.g., HD) may employ a timing information cable 204 or cable 200 configured for a lower resolution application or otherwise insufficient for the higher resolution application. By way of example, in various embodiments, a high resolution image capture device may utilize timing signals including high frequency clocks in a first, higher range of between about 30 MHz to about 60 MHz, or more. The encoded information, however, may be transmitted in a second, lower range of between about 1 MHZ to about 15 MHz (e.g., a nominal frequency of about 11 MHz). Thus, the timing information cable 204 (and thus cable 200) may be sized for the encoded signal, or sized for transmission of the second, lower range of frequencies, instead of being a larger size required for the first, higher range of frequencies.

Returning to FIG. 1, the depicted proximal end 110 includes an encoding module 111 and the display module 118. In some embodiments, the encoding module 111 and the display module 118 may be included in a single device or integral unit, while in other embodiments, the encoding module 111 and the display module 118 may be included in separate devices or units, for example separate devices or units that may communicably coupled via a wireless and/or hard wired connection. The display module 118 may include one or more of a screen, a light display, a speaker, or alarm, among others. Generally in various embodiments, the encoding module 111 may be configured to encode frame synchronizing information for controlling electronics (e.g., an image capture device) disposed proximate the distal end 140 of the system 100. For example, the encoding module 111 may be configured to encode frame synchronizing information into the timing information 160 to be transmitted via the cable 130. The timing information 160 may include a reference clock having a frequency lower than a frequency of the frame synchronizing information. Further, in various embodiments, the encoding module 111 may be configured to encode command information into the reference clock of the timing information 160. The command information, for example, may be configured for adjusting one or more settings of an image capture device or device disposed proximate the distal end 140. In various embodiments, the one or more settings may include, as examples, calibration control codes to adjust analog components, programming data for updating operating code of a controller at the distal end 140, or control codes for directing changes in specific modes of operation of an image capture device or module disposed proximate the distal end 140. In various embodiments, all or a portion of framing information to be encoded may be generated by the encoding module 111 (or one or more sub-modules thereof), or may be received by the encoding module 111.

In the illustrated embodiment, the encoding module 111 includes a reference clock module 112, a synchronization module 114, and a clock encoder module 116. Generally, in various embodiments, the clock encoder module uses information and/or signals from the reference clock module and the synchronization module 114 to produce an encoded signal that may be transmitted to the distal end 140. It may be noted that additional and/or other modules may be utilized in various embodiments. The reference clock module 112 in the illustrated embodiment is configured to provide a reference clock signal having a relatively low frequency relative to the framing information frequency to the clock encoder module 116. For example, a framing frequency may be an integer multiple of the frequency of a reference clock provided by the reference clock module 112. The synchronization module 114 is configured to provide synchronization information such as one or more signals and/or bits to the clock encoder module 116. The depicted clock encoder module 116 obtains the reference clock signal from the reference clock module 112 and the synchronization information from the synchronization module 114, and produces an encoded reference clock signal (e.g., timing information 160) from the obtained reference clock signal and synchronization information. For example, the encoded reference clock signal may include a reference clock signal encoded with information for framing, synchronization, and/or other control commands for use by the distal end 140. In various embodiments, framing, synchronization, and/or other control commands may be encoded into an encoded reference clock signal by one or more of omitting one or more periods from a reference clock signal, varying an amplitude (e.g., voltage) for one or more cycles of a reference clock signal, or varying a duty cycle of a reference clock signal, among others. The encoded reference clock signal may be transmitted to the distal end 140, and decoded at the distal end 140 to provided recovered framing information for driving or controlling an image capture device such as a CCD.

Various encoding schemes or techniques are discussed herein. The encoding schemes or techniques discussed herein are provided by way of example and are not intended to be exhaustive. For example, it should be noted that two or more of the encoding schemes or techniques discusses herein may be used in conjunction with each other. Further, it should be noted that additional or alternative encoding schemes or techniques may be employed in alternate embodiments.

Figure 3:
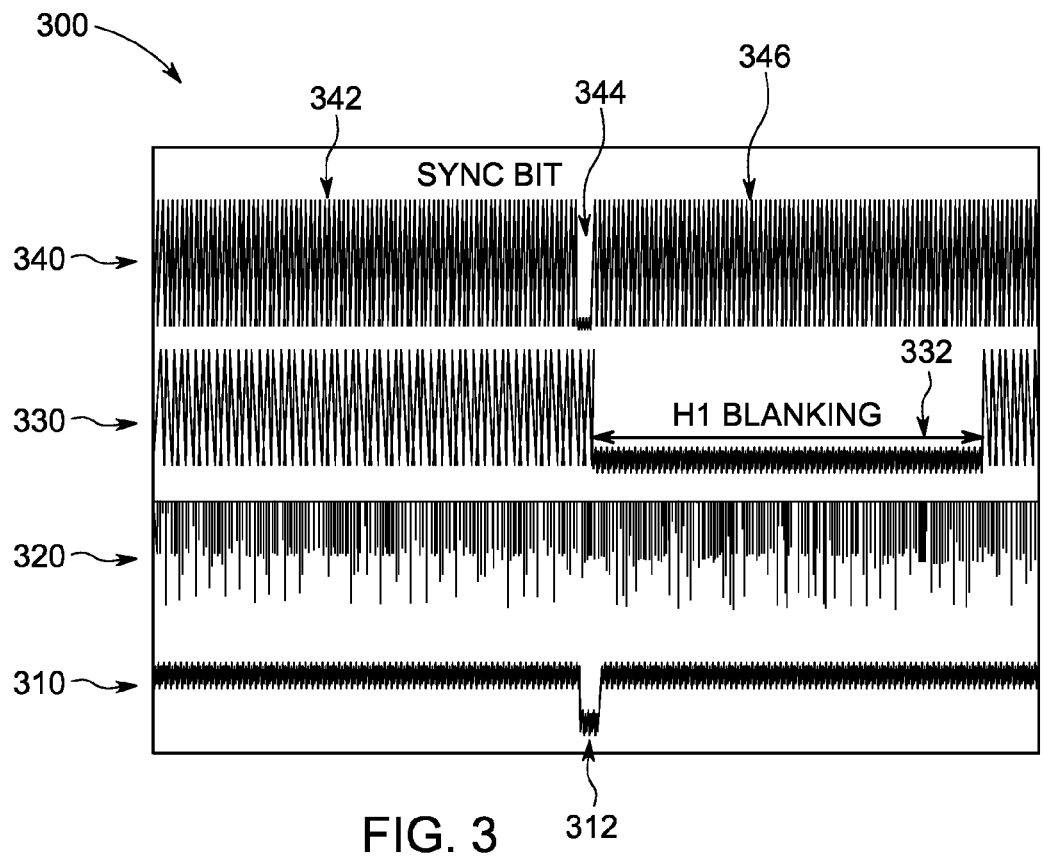
FIG. 3 is a view of an example of an encoding scheme in accordance with various embodiments.

FIG. 3 is one example of an encoding scheme 300. The encoding scheme 300 utilizes the omission of one or more cycles from an encoded reference clock signal to indicate a synchronization portion (e.g., a portion corresponding to a beginning or end of a blanking period associated with an endpoint of a line, or as another example, of a frame). The depicted encoding scheme includes a synchronization signal 310, a reset gate signal 320, a horizontal clock signal 330, and an encoded reference clock signal 340. The encoding scheme 300 may be employed to produce an encoded reference clock signal 340 using the synchronization signal 310, the reset gate signal 320, and the horizontal clock signal 330, and/or may be employed to obtain the synchronization signal 310, a reset gate signal 320, and/or horizontal clock signal 330 from a received encoded reference clock signal 340. Generally, the encoded reference clock signal 340 provides an encoded signal corresponding to the synchronization signal 310, the reset gate signal 320, and the horizontal clock signal 330. It may be noted that, in various embodiments, one or more vertical clock signals may also be utilized in the control of image capture. In some embodiments, a reference clock used for frame synchronization may have be faster (e.g., have a higher frequency) than the one or more vertical clocks.

In the illustrated embodiment, the synchronization signal 310 includes a synchronization portion 312. The depicted synchronization signal 310 is generally at a positive voltage for a majority of a duration, but drops to a lower voltage (e.g., about zero) during the synchronization portion 312. Other configurations may be employed in alternate embodiments. In the illustrated embodiments, the synchronization portion 312 corresponds to the beginning of a blanking period. In other embodiments, synchronization portions may additionally or alternatively correspond to the end of a blanking period. In various embodiments, blanking periods may correspond, for example, to the end of a line, or as another example, to the end of a frame. For example, in the illustrated embodiment, the horizontal clock signal 330 includes a blanking period 332, and the synchronization portion 312 of the synchronization signal 310 corresponds to the beginning of the blanking period 332 of the horizontal clock signal 330. In the illustrated embodiment, the blanking period 332 of the horizontal clock signal 330 is depicted as remaining low (e.g., at about zero volts) during the blanking period 332, but in other embodiments the blanking period 332 may be characterized by being at a high level of the horizontal clock signal 330. The reset gate signal 320 may have the same frequency as the horizontal clock signal 330, but be devoid of a blanking period. It may also be noted that an embedded imaging system may utilize more than one horizontal clock in various embodiments.

The encoded reference clock signal 340 includes a first portion 342, a synchronization bit 344, and a second portion 346. The first portion 342 corresponds to a portion of the horizontal clock signal 330 before the blanking period 332, the synchronization bit 344 corresponds to the synchronization portion 312 of the synchronization signal 310 (and thus also to the beginning of the blanking period 332), and the second portion 346 corresponds to the portion of the horizontal clock signal 330 after the beginning of the blanking period 332. The synchronization bit 344 of the illustrated embodiment includes a portion of the reference clock signal 340 where one or more cycles of the reference clock are omitted. The period of the encoded reference clock signal 340 may be determined by dividing the frequency of the horizontal clock signal 330 (or the reset gate signal 320) by an integer. Thus, the period of the encoded reference clock signal 340 sent via a cable from the proximal end to the distal end may be substantially lower than the frequency of a framing signal used to drive or control an image capture device, allowing use of a smaller diameter cable.

A distal end of an embedded imaging system that receives the encoded reference signal 340 may decode the encoded reference signal to provide recovered framing information, such as one or more of the synchronization signal 310, the reset gate signal 320, and the horizontal clock signal 330. For example, to obtain the frequency of the recovered framing information, the frequency of the encoded reference clock signal 340 may be multiplied by an appropriate integer value, for example using a phase locked loop (PLL) disposed proximate the distal end. By way of example, an 11 MHz reference clock signal may be used to provide a 44 MHz high frequency clock for clocking an HD image capture device. In various embodiments, even higher frequency outputs (e.g., 8 times a reference clock frequency) may be utilized. Also, to provide frame synchronized clocking signals (e.g., blanking) for the image device, the distal end may be configured to use synchronization information encoded into the encoded reference clock signal 340. For example, the distal end may include a Programmable Logic Device (PLD) that uses the output of the PLL along with recovered synchronization information from the encoded reference clock signal 340 (e.g., information corresponding to the synchronization bit 344) to generate frame synchronized clocking signals. For example, a blanking period may be determined to have a start corresponding to the location of the synchronization bit 344 and to have a predetermined duration. As another example, a blanking period may be determined to have a start corresponding to a location of a first synchronization bit and to have an end corresponding to a location of a second synchronization bit. In various embodiments, a distal end of an imaging system may alternatively or additionally use a field-programmable gate array (FPGA) or an application specific integrated circuit (ASIC) for recovering synchronization information and/or providing frame synchronized clocking signals for use by an image capture device such as a CCD. Thus, in various embodiments, relatively high frequency framing (or synchronized clocking) information or signals may be encoded by omitting one or more cycles of a relatively low frequency reference clock. One potential drawback of such an encoding scheme is that, in various embodiments using a PLL to decode the encoded reference clock, the omitted cycles may cause difficulties or issues with the PLL and/or the frequency generated by the PLL.

Figure 4:
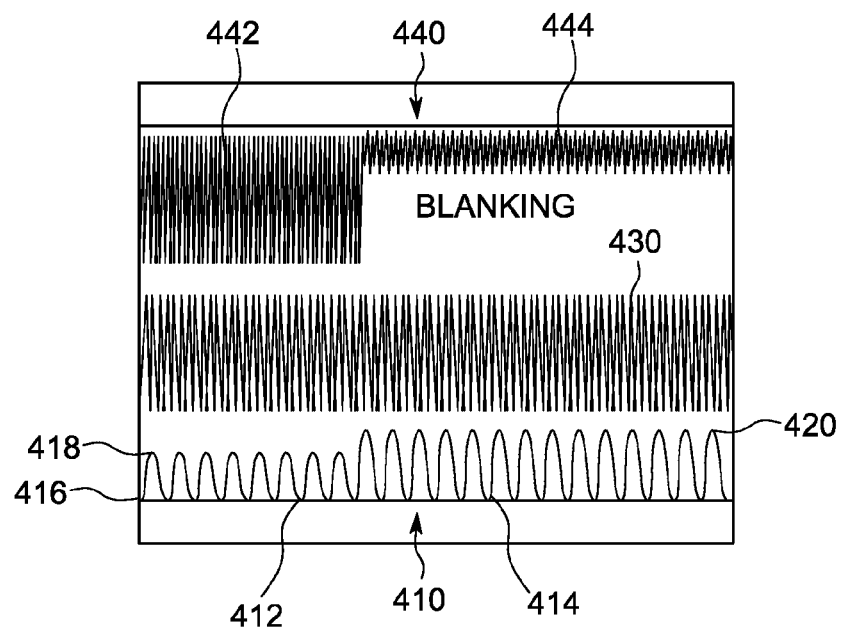
FIG. 4 is a view of an example of another encoding scheme in accordance with various embodiments.

In various embodiments, other encoding schemes that do not drop or omit cycles of an encoded reference clock may be employed. FIG. 4 illustrates an encoding scheme 400. The encoding scheme 400 does not drop cycles from an encoded reference clock. As shown in FIG. 4, the encoding scheme 400 utilizes multiple voltage levels. In the embodiment depicted in FIG. 4, the encoding scheme 400 includes an encoded reference clock 410, a reset gate 430, and a horizontal clock 440.

The encoded reference clock 410 includes three voltage levels, namely a low voltage 416, an intermediate voltage 418, and a high voltage 420. The low voltage, for example may be about zero volts. In the illustrated embodiment, the intermediate voltage 418 may be understood as a first level or state of the encoded reference clock 400, and the high voltage 420 may be understood as a second level or state of the encoded reference clock. Thus, the encoded reference clock 420 may be understood as a multi-level clock. In various embodiments, encoded reference clocks may employ additional voltage levels. In some embodiments, the intermediate voltage 418 may be about 1.25 volts and the high voltage 420 may be about 3.3 volts. As another example, in various embodiments, the intermediate voltage 418 may be about 3.3 volts and the high voltage 420 may be about 5 volts. In various embodiments, a multi-level clock signal may be created using standard logic level signals which are summed in the analog domain using an op-amp.

Generally, in various embodiments, the encoded reference clock 410 may configured as a wave (e.g., a square wave or a sine wave, among others) alternating between the low voltage 416 and one of the intermediate voltage 418 or the high voltage 420 at a regular rate that may be understood as the reference clock frequency. Synchronization events (e.g., blanking periods) and/or commands for one or more aspects of image collection at a distal end may be encoded into the encoded reference clock 410 via the selection of and/or variations in which of the intermediate voltage 418 and the high voltage 420 is alternated between with the low voltage 416. For example, in the embodiment depicted in FIG. 4, the encoded reference signal 400 includes a first portion 412 and a second portion 414. The first portion 412 alternates at the reference clock frequency between the low voltage 416 and the intermediate voltage 418, and corresponds to a portion of the horizontal clock 440 having values alternating between a high and low voltage at a framing frequency (e.g., a frequency provided by multiplying the reference clock frequency by an integer). The second portion 414 alternates at the reference clock frequency between the low voltage 416 and the high voltage 420, and corresponds to a blanking portion of the horizontal clock 440. Thus, in the illustrated embodiment, a blanking period for the horizontal clock 440 is encoded in the encoded reference clock via the high voltage 420. In the illustrated embodiment, as long as the encoded reference clock continues to utilize the high voltage 420, the horizontal clock 440 is maintained in a blanking period. Other arrangements may be employed in alternate embodiments. As just one example, a single cycle (or other predetermined number of cycles) utilizing the high voltage 420 may signal the beginning and/or end of a blanking period.

The encoding scheme 400 depicted in FIG. 4 includes a reset gate 430. The reset gate 430 as shown in FIG. 4 alternates between a low and a high voltage and a generally constant rate. The generally constant rate, for example, may be obtained by applying a multiple to the frequency of the encoded reference clock 410. For example, a distal end may include a PLL (or other circuit and/or device) configured to output a signal having a frequency that is an integer multiple of an input frequency (e.g., a frequency obtained from an encoded reference clock signal). Thus, a distal end of an imaging system may receive the encoded reference clock 410 and produce the reset gate 430 using the encoded reference clock 410.

The encoding scheme 400 depicted in FIG. 4 also includes a horizontal clock 440. The horizontal clock 440 may have a similar frequency as the reset gate 430, which may obtained by applying a multiple to the frequency of the encoded reference clock 410. The horizontal clock 440 as shown in FIG. 4 includes a clocking portion 442 and a blanking portion 444. The clocking portion may alternate between a high and a low voltage at a regular frequency (e.g., the same frequency as the reset gate 430 and a multiple of the frequency of the encoded reference clock 410). In the embodiment illustrated in FIG. 4, the horizontal clock 440 may be understood as blanking high, as the blanking period 444 occurs at the higher voltage of the horizontal clock 440. The horizontal clock 440 may be constructed by applying a multiplier to the frequency of the encoded reference clock 410 to obtain the frequency for the clocking period 442, and by generating the blanking period 444 when the encoded reference clock 410 is at a state or level corresponding to the high voltage 420.

For example, in various embodiments, a PLD (or other device and/or circuit) may include comparators and/or multi-level logic family input buffers which are configured to operate at different voltage levels corresponding of the voltage levels or states of a multi-level clock. For example, a first buffer may be set to trigger at 1.25 volts to support a first bus family while a second buffer is configured to trigger at 3.3 volts to support a second bus family. The same signal may be fed into both buffers, with only the first buffer triggering during the non-blanking section of the reference clock signal (e.g., the intermediate voltage level 418 depicted in FIG. 4, while the second buffer triggers only during the blanking mode section (e.g., the high voltage level 420 depicted in FIG. 4). The reference rate constant clock may be fed directly into, for example, a PLL to generate higher frequency clocks to operate a CCD.

Figure 5:
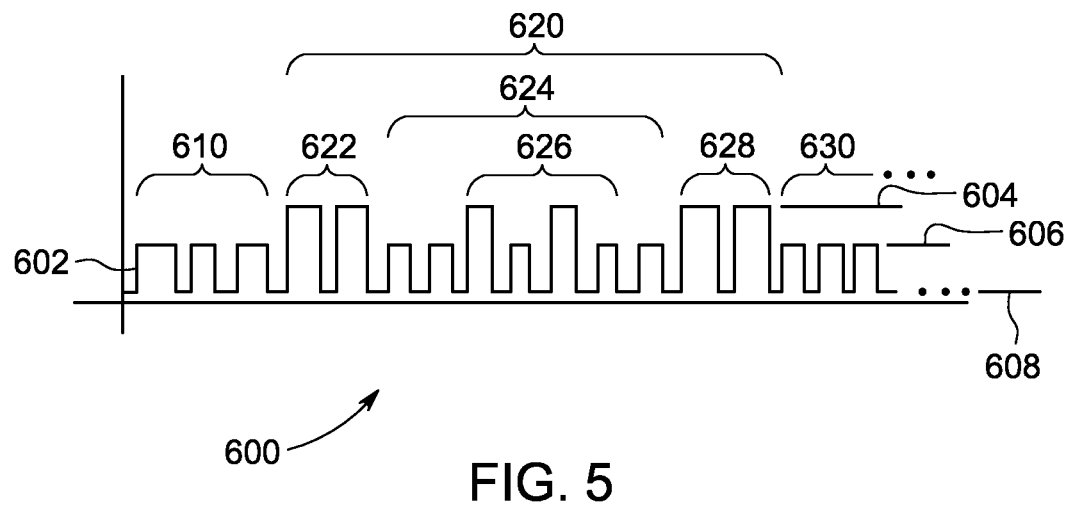
FIG. 5 is a view of an example of another encoding scheme in accordance with various embodiments.

One advantage of such an encoding scheme, such as the encoding scheme 400, that does not drop cycles to encode synchronization information but instead utilizes multiple voltage levels to encode synchronization information is that a PLL frequency obtained from such an encoded signal has reduced or eliminated shifting because there are no missing periods. FIG. 5 illustrates an example encoding scheme 600 that utilizes one or more cycles to encode a beginning of a synchronization event (e.g., a blanking period) and one or more cycles to encode an end of a synchronization event, without an encoded reference clock remaining at a high state throughout the blanking period. In the illustrated embodiment, the beginning and end of a synchronization event are encoded via two consecutive cycles at a high voltage level or state. Other encoding schemes may be employed in alternate embodiments.

The encoding scheme 600 depicted in FIG. 5 includes an encoded reference clock 602 including a first clocking period 610, a blanking period 620, and a second clocking period 630. The encoded reference clock 602 depicted in FIG. 5 includes a signal that varies between a low voltage level 608, an intermediate voltage level 606, and a high voltage level 604. The low voltage level 608, for example, may be about zero volts. The first clocking period 610 corresponds to a clocking period and is encoded by a regular variation between the low voltage level 608 and the intermediate voltage level 606 at a reference clock frequency. The blanking period 620 corresponds to an encoded blanking period, and includes a beginning portion 622, an intermediate portion 624, and an end portion 628. Both the beginning portion 622 and the end portion 628 include 2 consecutive cycles alternating between the low voltage level 608 and the high voltage level 604 at the reference clock frequency. In alternate embodiments, each may be encoded via a single cycle at the high voltage level 604. In still other embodiments, for example to improve robustness of an encoding scheme, each transition or end point of a synchronization event (e.g., beginning of a blanking period, ending of a blanking period) may be encoded using a unique series of high and intermediate voltage cycles. For example, with a high voltage cycle corresponding to a "1" and an intermediate voltage cycle corresponding to a "0," the beginning of a blanking period may be encoded as "1, 0, 1, 1, 0, 1, 1" and the end of a blanking period may be encoded as "1, 1, 0, 0, 1, 1, 1."

The intermediate portion 624 of the blanking period is interposed between the beginning portion 622 and the end portion 628, and includes an encoded command portion 626. The encoded command portion 626 includes a predetermined pattern of cycles corresponding to the intermediate voltage level 606 and the high voltage level 604 configured to encode a command or setting. In various embodiments, the one or more settings may include, as examples, calibration control codes to adjust analog components, programming data for updating operating code of a controller, or control codes for directing changes in specific modes of operation of an image capture device. In the illustrated embodiment, the encoded command portion 626 of the blanking portion 620 includes four cycles, namely, a first high voltage cycle followed by a second intermediate voltage cycle, which is followed by a third high voltage cycle, which is followed by a fourth intermediate cycle. The sequence of intermediate and high voltages may be used to encoded a command word that may be recognized and implement by the distal end receiving an encoded reference clock signal including the encoded word during a blanking period. For example, if the intermediate voltage is considered a "0" and the high voltage considered a "1," the depicted encoded command portion 626 may be understood as including a code word corresponding to "1010." Other commands may be encoded using different combinations of high and intermediate voltage cycles. In the illustrated embodiment, a single encoded command portion or code word is illustrated; however, in various embodiments, plural encoded command portions or code words may be employed. The second clocking period 630 follows the blanking portion 620, and corresponds to a clocking period. The second clocking period 630, like the first clocking period 610, may be encoded by a regular variation between a low and intermediate voltage at a reference clock frequency. In other embodiments, for example, the blanking period may have a predetermined duration, and a counter may be initiated after the beginning of the blanking period, with the blanking period ending (and the second clocking period 630 beginning) after the counter expires.

A distal end may include one or more components or modules (e.g., PLD, PLL, FPGA, or ASIC, among others) configured to decode the encoded reference clock 602 and provide clocking and framing information for controlling or driving an image capture device such as a CCD. For example, a distal end may receive the encoded reference clock 602 configured via the encoding scheme 600 and provide a reset gate and one or more horizontal clocks having a frequency that is faster or at a higher rate by an integer multiple than the frequency of the encoded reference clock 602 (e.g., via a PLL). The distal end may then initiate a blanking period in one or more horizontal clocks based on the appearance of the beginning portion 622 of the blanking portion 620, and terminate the blanking period based on the appearance of the end portion 628 of the blanking portion 620. Further, the distal end may recognize and implement one or more commands (e.g., settings changes) based on one or more encoded command portions 626.

Figure 6:
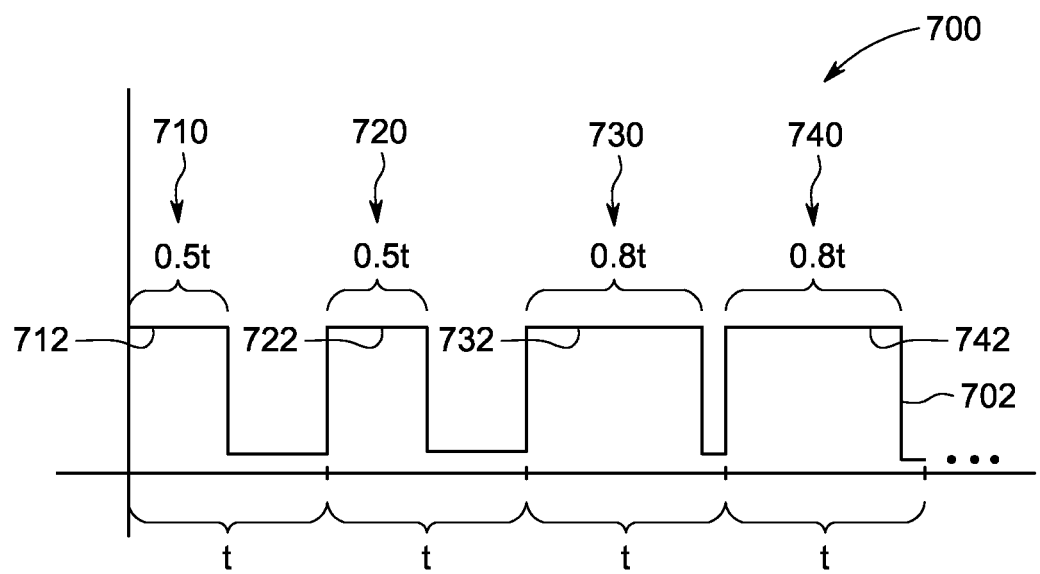
FIG. 6 is a view of an example of another encoding scheme in accordance with various embodiments.

FIG. 6 illustrates an example encoding scheme 700 that utilizes a change in duty cycle of an encoded reference clock 702 to communicate synchronization and/or command information. For example, a frequency of the encoded reference clock 702 may be multiplied to obtain a frequency for a horizontal clock and a reset gate, and variations in duty cycle may be used to identify synchronization events (e.g., beginning and/or end of a blanking period). A duty cycle may be understood as the percent of time that an entity spends in an active state as a fraction of a total time. In the illustrated embodiment, the duty cycle corresponds to the amount of time the encoded reference clock 702 is at a higher voltage state for a given cycle.

The illustrated encoded reference clock 702 includes a first cycle 710, a second cycle 720, a third cycle 730, and a fourth cycle 740. Each cycle has a duration or period of t, with the frequency of the encoded reference clock 702 therefore 1/t. The first cycle 710 includes a duty cycle 712 having a duration of 0.5t, the second cycle 720 includes a duty cycle 722 having a duration of 0.5t, the third cycle 730 includes a duty cycle 732 having a duration of 0.8t, and the fourth cycle 740 includes a duty cycle 742 having a duration of 0.8t. The frequency of a high frequency clock for driving or controlling an image capture device may be obtained by multiplying the frequency of the encoded reference clock 702 by a predetermined integer multiple, and synchronization events (e.g., blanking periods) may be determined based on duty cycle duration. For example, the transition from a duty cycle of 0.5t to a duty cycle of 0.8t at the third cycle 730 may, in some embodiments, be used to indicate the beginning of a blanking period. A corresponding recovered clock may be remain in a blanking mode, as one example, as long as the duty cycle remains at 0.8t. As another example, the beginning of a blanking period may be indicated by the transition to a duty cycle of 0.8t, and the duration of the blanking period may be determined using a counter. Alternatively or additionally, variations in duty cycles may be arranged in predetermined series to provide a code word or command corresponding to a beginning of a blanking period, an end of a blanking period, or a command to change a setting of an image capture device, among others.

Returning to FIG. 1, the depicted distal end 140 includes an imaging module 141 that in turn includes an image capture device 148 and a decoding control module 142. In the illustrated embodiment, the image capture device 148 is configured to obtain imaging information of at least a portion of the volume of interest 102. Generally, in various embodiments, the image capture device 148 is configured to obtain imaging information that may be transmitted to the proximal end 110 via the cable 130 for further processing and/or display. The image capture device 148 in some embodiments may include a CCD. Other types of image capture devices may be employed in alternate embodiments.

Generally, the decoding control module 142 may be configured to obtain timing information (e.g., to receive an encoded reference clock signal from the proximal end 110 via the cable 130), to decode the timing information to obtain recovered frame synchronizing information corresponding to frame synchronizing information encoded by the encoding module 111 of the proximal end 110, and to control the image capture device 148 using the recovered frame synchronizing information. The decoding control module 142 may alternatively or additionally be configured to obtain command information from the timing information. For example, the decoding control module 142 may be configured also decode and apply command information, for example, to adjust one or more settings of the image capture device 148. In various embodiments, the distal end 140 may have a reduced sized and/or reduced cost facilitated by the relative ease or simplicity of decoding the framing information compared to the initial generation of the framing information.

In the illustrated embodiment, the decoding control module includes a PLL module 144 and a PLD module 146. The PLL module 144 is an example of a frequency decoding module, and the PLD module is an example of a synchronization decoding module 146. Generally, in various embodiments, the PLL module 144 is configured to provide a frequency for one or more clocks to the image capture device 148 using an encoded reference clock signal obtained from the proximal end 110, and the PLD module 146 is configured to provide information to the image capture device 148 for synchronization events using an encoded reference clock obtained from the proximal end 110.

In the illustrated embodiment, the PLL module 144 includes a phase locked loop configured to apply a multiple to the frequency of the reference clock of the timing information to obtain the frequency of the frame synchronizing information. The frequency of the frame synchronizing information, for example, may be used as the frequency of a reset gate as well as one or more horizontal clocks utilized in conjunction with the image capture device 148. Other circuits or devices may be employed in frequency decoding modules (the PLL module 144 is an example of a frequency decoding module) in other embodiments.

The depicted PLD module 146 includes a PLD and is configured to identify or obtain one or more synchronization events from the timing information (e.g., an encoded reference clock) obtained via the cable 130 from the proximal end 110. The PLD module 146 may be configured to identify omitted cycles, variations in amplitude (e.g., voltage), or variations in duty cycle, among others, in the obtained timing information, and to determine encoded synchronization events (e.g., blanking periods, beginning of a blanking period, end of a blanking period) and/or control or settings commands for the image capture device 148 using the identified omitted cycles, variations in amplitude (e.g., voltage), variations in duty cycle, or the like from the obtained timing information. In various embodiments, the PLD module 146 may include comparators and/or multi-level logic family input buffers which are configured to operate at different voltage levels corresponding to the voltage levels or states of a multi-level clock. Other circuits or devices (e.g., one or more ASICs or FPGAs, among others) may be employed in synchronization decoding modules (the PLD module 146 is an example of a synchronization decoding module) in other embodiments.

Figure 7:
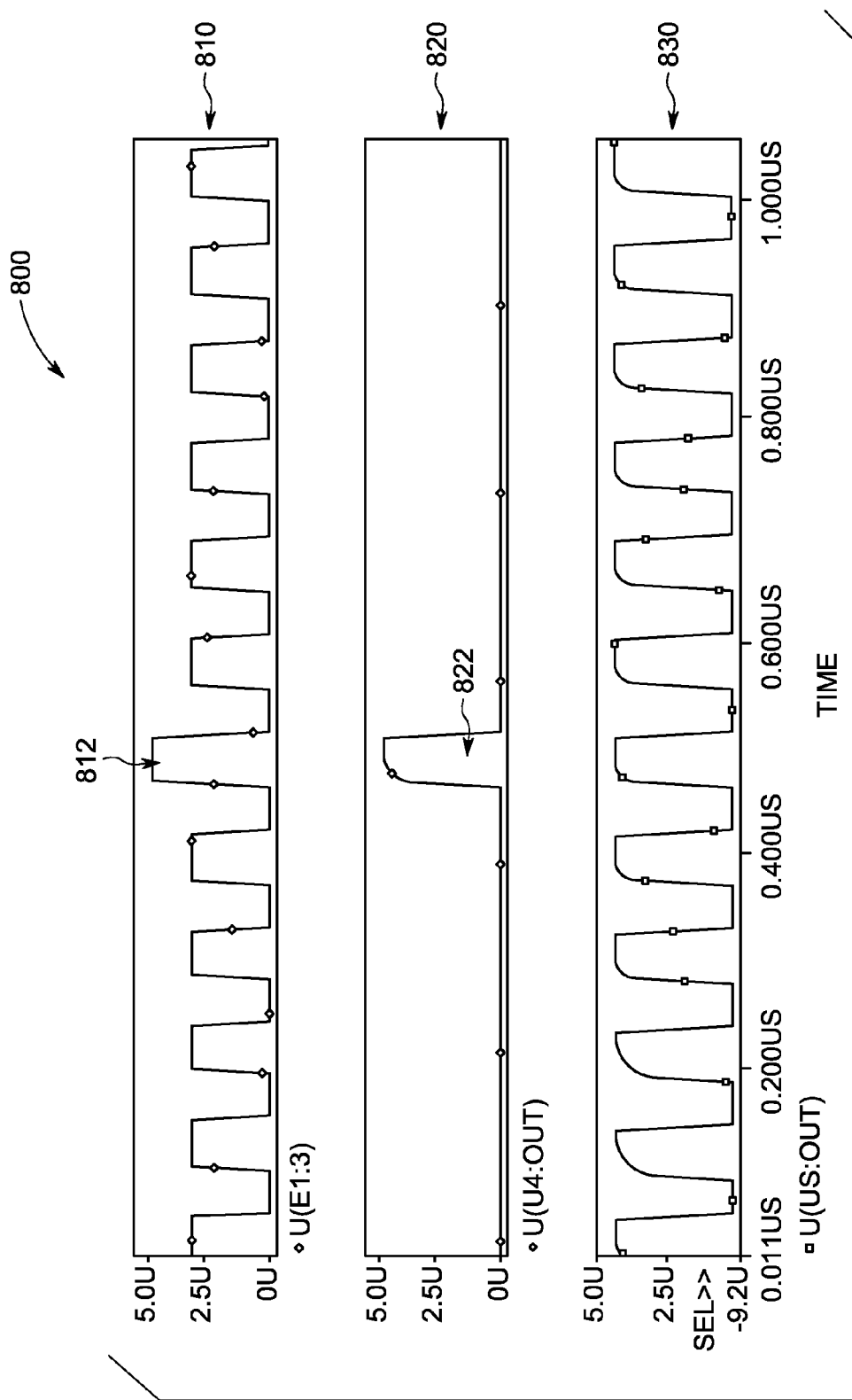
FIG. 7 is a view of an example of another encoding scheme in accordance with various embodiments.

FIG. 7 illustrates an encoding scheme 800 formed in accordance with various embodiments, and provides an example of the operation of a decoding and control module (e.g., decoding control module 142). The encoding scheme 800 includes an encoded reference clock 810, a recovered synchronization signal 820, and a recovered reference clock 830. Generally, the encoded reference clock 810 may be transmitted from the proximal end (e.g., the proximal end 110) to the distal end (e.g., the distal end 140), and decoded by the decoding control module of the distal end. In the illustrated embodiments, the decoding control module may use the encoded reference clock 810 to determine, produce, or otherwise obtain the recovered synchronization signal 820 and the recovered reference clock 830, and use the recovered synchronization signal 820 and the recovered reference clock 830 to determine, produce, or otherwise obtain recovered frame synchronizing information (e.g., a horizontal clock used to drive or control an image capture device).

In the illustrated embodiment, the encoded reference clock 810 includes a synchronization bit 812 that identifies a timing of a synchronization event (e.g., the beginning of a blanking period. The synchronization bit 812, for example, may be encoded via a change in amplitude (e.g., voltage) of a regularly occurring waveform of the encoded reference clock having a reference clock frequency. The encoded reference clock, for example, may be transmitted from the proximal end 110 to the distal end 140 via the cable 130 (e.g., via a timing information cable such as timing information cable 204). The decoding control module 142 may obtain the encoded reference clock 810. The PLD module 146 may be employed to identify the synchronization bit 812 and to produce a synchronization signal 820 including a recovered synchronization bit 822. The decoding control module 142 may also use the reference clock frequency of the encoded reference clock 810 to produce a recovered reference clock 830 configured as a regularly occurring waveform having the reference clock frequency. The PLL module 144 may then be employed to multiply the reference clock frequency (e.g., by an integer) to obtain a frequency for one or more higher frequency clock signals (not shown in FIG. 7). Synchronization events may be combined with a higher frequency clock signal to provide, for example, a horizontal clock signal including one or more blanking periods used to control or drive the image capture device 148.

Figure 8:
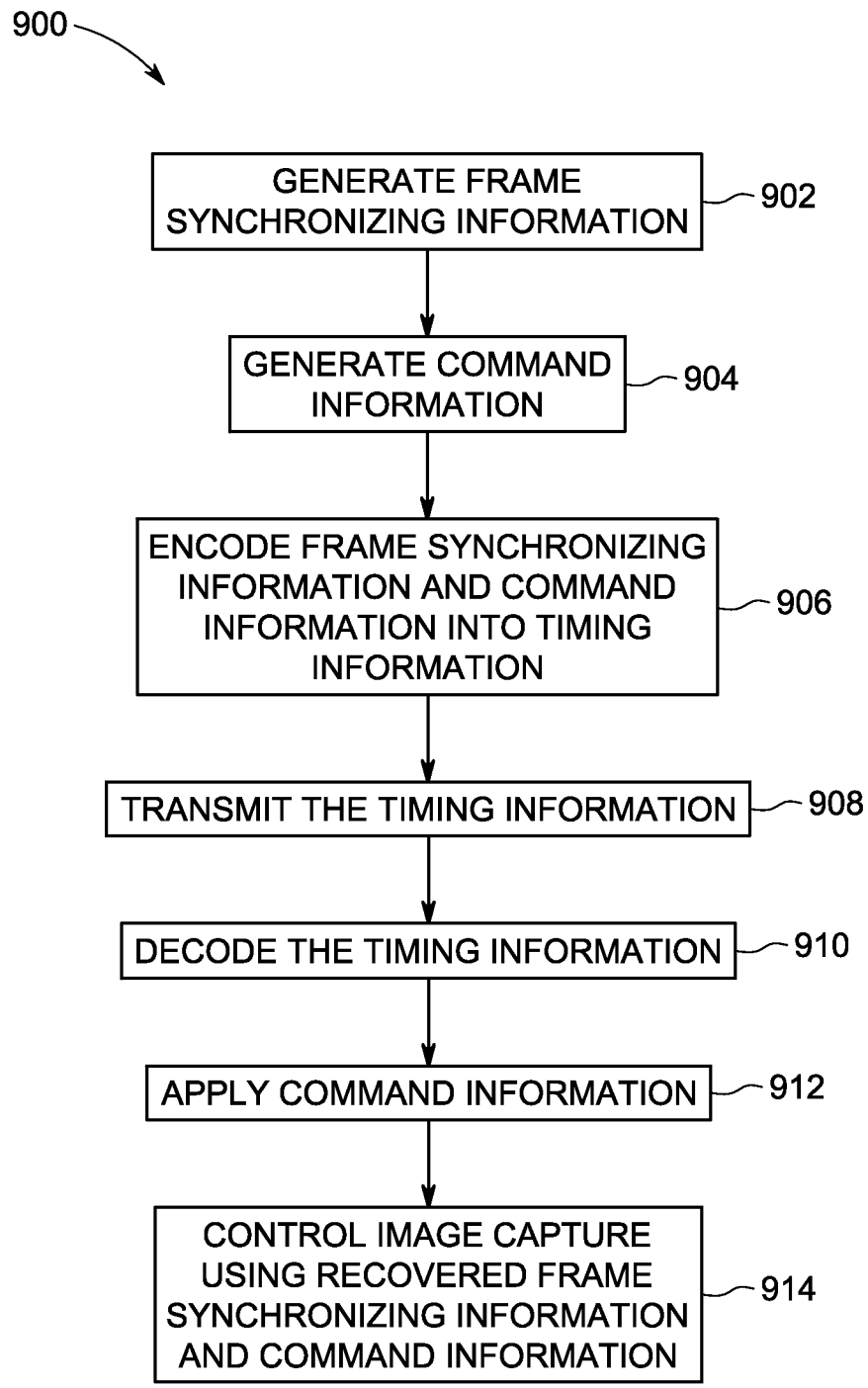
FIG. 8 is a flowchart of a method for obtaining imaging information of a volume of interest.

FIG. 8 provides a flowchart of a method 900 for obtaining imaging information using an embedded imaging system, such as a boroscope. In various embodiments, the method 900, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

At 902, frame synchronizing information is generated, for example, using one or more processors disposed on a proximal portion of an embedded imaging system (e.g., a portion that will not be inserted into a volume of interest at least a portion of which is to be imaged). The frame synchronizing information may be configured to drive a solid state image capture device such as CCD. In various embodiments, the frame synchronizing information may include blanking information, and may be used to group or organize lines or pixels gathered at one or more given times with other appropriate lines or pixels. The image capture device may be disposed on a distal portion of the embedded imaging system (e.g., a portion that will be inserted into the volume of interest during imaging).

At 904, command information is generated, for example, using one or more processors disposed on the proximal portion of the embedded imaging system. The command information in various embodiments may be configured to adjust analog components of the distal portion associated with imaging, to provide programming data for updating operating code of a controller at the distal portion, to provide calibration control, or, as another example, to provide control codes for directing changes in specific modes of operation of one or more distally located state machines (e.g., a CCD). It may be noted that command information as used herein is fundamentally different than frame synchronizing information and does not include framing information or other timing information for driving an image acquisition process.

At 906, the frame synchronizing information and command information are encoded into timing information. The timing information may include, for example a reference clock including one or more encoded synchronization events and/or commands. In various embodiments, the reference clock is at a substantially lower frequency (e.g., 50% or less) than the frequency of the frame synchronizing information, and thus may utilize a smaller diameter cable (or portion of a cable) for transmission from the proximal portion to the distal portion. In various embodiments, more than one set of frame synchronizing information may be generated and encoded (e.g., more than one horizontal clock). In some embodiments, only frame synchronizing information may be encoded into the timing information, while in other embodiments command information may also be encoded into the timing information (e.g., encoded using one or more predetermined series or code words including during a blanking period or portion of an encoded reference clock). In various embodiments, the frame synchronizing information (and/or command information) may be encoded using one or more of an omission of cycles, a variation in a peak amplitude or voltage of a signal (e.g., a multi-level clock), or a variation in duty cycle, among others. For example, in some embodiments encoding the frame synchronizing information into the timing information may include encoding the frame synchronizing information using at least a low voltage, an intermediate voltage, and a high voltage for the reference clock of the timing information.

At 908, the timing information is transmitted from the proximal portion (where the timing information was encoded) of the embedded imaging system to the distal portion (where the timing information is to be decoded for use in controlling or driving image capture). The timing information may be transmitted via a cable. Because the timing information is at a substantially lower frequency than the frame synchronizing information, a substantially smaller diameter cable may be employed to transmit the timing information than would be required if transmitted at the higher frequency of the frame synchronizing information. Additionally or alternatively, because frame synchronizing information may be obtained at the distal end by merely decoding the timing signal instead of initially generating the frame synchronizing information, the size, cost, complexity, and/or processing requirements of the distal portion may be reduced in comparison to designs that would require initial generation of the frame synchronizing information at the distal portion.

At 910, the timing information is decoded, for example, by one or more processors disposed on the distal portion of the embedded imaging system. In various embodiments, the timing information may be decoded to obtain recovered frame synchronizing information corresponding to the frame synchronizing information encoded at the proximal portion and transmitted to the distal portion. For example, in some embodiments, a PLD or other device or circuit may be used to identify blanking or other synchronization information (and/or command information), and a PLL or other circuit or device may be used to multiply a reference frequency from an encoded reference clock of the obtained timing information to obtain a recovered signal (or signals) having a higher frame synchronizing frequency.

At 912, the command information is applied. For example, one or more settings or adjustments may be made to components at the distal portion using command information recovered from the timing information (e.g., from an encoded reference clock).

At 914, image capture is controlled using the recovered frame synchronizing information (e.g., the information recovered via the decoding at 910). In the illustrated embodiment, image capture is also controlled using the recovered frame synchronizing information as well as command information. For example, a horizontal clock at the frame synchronizing frequency including blanking periods determined from the encoded reference clock transmitted to the distal portion may be used to drive or control an image capture device, such as a CCD. The image capture device may be positioned or disposed on the proximal portion inside a volume of interest, and may be transmit imaging information to a display module disposed on the proximal portion outside of the volume of interest, allowing an observer outside of the volume of interest to view imaging information of at least a portion of an interior of the volume of interest.

Thus, for example, in various embodiments, one or more clocks at a higher frequency for high resolution may be generated at a proximal end, and encoded into a lower frequency encoded signal at the proximal end, allowing for a smaller diameter cable for transmission of the encoded signal from the proximal end to the distal end. The encoded signal may then be transmitted to the distal end. Once obtained by the distal end, the encoded signal may then be decoded into one or more higher frequency clocks for use in controlling an image capture device. After the image capture device has obtained imaging information, the imaging information may be transmitted to the proximal end for processing and/or display.

It should be noted that the particular arrangement of components (e.g., the number, types, placement, or the like) of the illustrated embodiments may be modified in various alternate embodiments. In various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), a given module or unit may be added, or a given module or unit may be omitted.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and the like. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An embedded imaging system comprising:
an encoding module disposed proximate to a proximal end of the system, the encoding module configured to encode frame synchronizing information for controlling electronics disposed proximate a distal end of the system, the encoding module configured to encode the frame synchronizing information into timing information comprising a reference clock;
an imaging module disposed proximate the distal end, the imaging module comprising:
an image capture device configured to obtain imaging information of at least a portion of the volume of interest; and
a decoding control module configured to obtain the timing information, to decode the timing information to obtain recovered frame synchronizing information corresponding to the frame synchronizing information encoded by the encoding module, and to control the image capture device using the recovered frame synchronizing information; and
a cable interposed between the proximal end and the distal end, the cable configured for passage therethrough of the timing information from the proximal end to the distal end, and for passage therethrough of the imaging information from the distal end to the proximal end, wherein the timing information includes blanking information encoded using a removal of predetermined periods in the reference clock of the timing information.

2. The embedded imaging system of claim 1, wherein the decoding control module comprises a phase locked loop configured to apply a multiple to a frequency of the reference clock of the timing information to obtain a frequency of the frame synchronizing information.

3. The embedded imaging system of claim 1, wherein the encoding module is configured to encode the frame synchronizing information using at least a low voltage, an intermediate voltage, and a high voltage for the reference clock of the timing information, wherein the reference clock is configured as a multi-level clock.

4. The embedded imaging system of claim 3, wherein the timing information includes blanking information encoded as a contiguous series of clock periods using one of the high voltage or the intermediate voltage.

5. The embedded imaging system of claim 3, wherein the timing information includes blanking information encoded as at least one of a predetermined number or pattern of clock periods using at least one of the high voltage or the intermediate voltage, and wherein the decoding control module comprises at least one counter to generate the recovered frame synchronizing information using the at least one of a predetermined number or pattern of clock periods using the at least one of the high voltage or the intermediate voltage.

6. The embedded imaging system of claim 3, wherein the timing information includes blanking information corresponding to a beginning and an end of a blanking period, wherein a first at least one clock period using at least one of the high or intermediate voltage corresponds to the beginning of the blanking period and a second at least one clock period using the one of the at least one high voltage or the intermediate voltage corresponds to the end of the blanking period.

7. The embedded imaging system of claim 1, wherein the timing information includes at least one of blanking information or command information encoded using a variation in a duty cycle of the reference clock of the timing information.

8. The embedded imaging system of claim 1, wherein the image capture device comprises a charge coupled device (CCD).

9. The embedded imaging system of claim 1, wherein the encoding module is further configured to encode command information into the reference clock of the timing information for adjusting one or more settings of the image capture device.

10. The embedded imaging system of claim 1, wherein the reference clock has a frequency lower than a frequency of the frame synchronizing information.

11. An embedded imaging system comprising:
an encoding module disposed proximate to a proximal end of the system, the encoding module configured to encode frame synchronizing information for controlling electronics disposed proximate a distal end of the system, the encoding module configured to encode the frame synchronizing information into timing information comprising a reference clock, wherein the encoding module is configured to encode the frame synchronizing information using at least a low voltage, an intermediate voltage, and a high voltage for the reference clock of the timing information, wherein the reference clock is configured as a multi-level clock, wherein the timing information includes blanking information encoded as a contiguous series of clock periods using one of the high voltage or the intermediate voltage;

an imaging module disposed proximate the distal end, the imaging module comprising:

an image capture device configured to obtain imaging information of at least a portion of the volume of interest; and a decoding control module configured to obtain the timing information, to decode the timing information to obtain recovered frame synchronizing information corresponding to the frame synchronizing information encoded by the encoding module, and to control the image capture device using the recovered frame synchronizing information; and a cable interposed between the proximal end and the distal end, the cable configured for passage therethrough of the timing information from the proximal end to the distal end, and for passage therethrough of the imaging information from the distal end to the proximal end.

12. An embedded imaging system comprising:

an encoding module disposed proximate to a proximal end of the system, the encoding module configured to encode frame synchronizing information for controlling electronics disposed proximate a distal end of the system, the encoding module configured to encode the frame synchronizing information into timing information comprising a reference clock, wherein the encoding module is configured to encode the frame synchronizing information using at least a low voltage, an intermediate voltage, and a high voltage for the reference clock of the timing information, wherein the reference clock is configured as a multi-level clock, wherein the timing information includes blanking information encoded as at least one of a predetermined number or pattern of clock periods using at least one of the high voltage or the intermediate voltage, and wherein the decoding control module comprises at least one counter to generate the recovered frame synchronizing information using the at least one of a predetermined number or pattern of clock periods using the at least one of the high voltage or the intermediate voltage;

an imaging module disposed proximate the distal end, the imaging module comprising:

an image capture device configured to obtain imaging information of at least a portion of the volume of interest; and a decoding control module configured to obtain the timing information, to decode the timing information to obtain recovered frame synchronizing information corresponding to the frame synchronizing information encoded by the encoding module, and to control the image capture device using the recovered frame synchronizing information; and a cable interposed between the proximal end and the distal end, the cable configured for passage therethrough of the timing information from the proximal end to the distal end, and for passage therethrough of the imaging information from the distal end to the proximal end.

13. An embedded imaging system comprising:

an encoding module disposed proximate to a proximal end of the system, the encoding module configured to encode frame synchronizing information for controlling electronics disposed proximate a distal end of the system, the encoding module configured to encode the frame synchronizing information into timing information comprising a reference clock, wherein the encoding module is configured to encode the frame synchronizing information using at least a low voltage, an intermediate voltage, and a high voltage for the reference clock of the timing information, wherein the reference clock is configured as a multi-level clock, wherein the timing information includes blanking information corresponding to a beginning and an end of a blanking period, wherein a first at least one clock period using at least one of the high or intermediate voltage corresponds to the beginning of the blanking period and a second at least one clock period using the one of the at least one high voltage or the intermediate voltage corresponds to the end of the blanking period;

an imaging module disposed proximate the distal end, the imaging module comprising:

an image capture device configured to obtain imaging information of at least a portion of the volume of interest; and a decoding control module configured to obtain the timing information, to decode the timing information to obtain recovered frame synchronizing information corresponding to the frame synchronizing information encoded by the encoding module, and to control the image capture device using the recovered frame synchronizing information; and a cable interposed between the proximal end and the distal end, the cable configured for passage therethrough of the timing information from the proximal end to the distal end, and for passage therethrough of the imaging information from the distal end to the proximal end.

\* \* \* \* \*